(12) United States Patent
Mattern

(10) Patent No.: US 8,198,608 B2
(45) Date of Patent: Jun. 12, 2012

(54) REDUCING THE WIDENING OF A RADIATION BEAM

(75) Inventor: Detlef Mattern, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 210 days.

(21) Appl. No.: 12/617,505

(22) Filed: Nov. 12, 2009

(65) Prior Publication Data

US 2010/0181494 A1 Jul. 22, 2010

(30) Foreign Application Priority Data

Nov. 20, 2008 (DE) .......................... 10 2008 058 299

(51) Int. Cl.
*A61N 5/00* (2006.01)
(52) U.S. Cl. .................................. 250/492.1; 250/492.3
(58) Field of Classification Search ............... 250/492.1, 250/492.3
See application file for complete search history.

(56) References Cited

U.S. PATENT DOCUMENTS 6,485,007 B1 * 11/2002 Duelli ........................... 267/164
7,385,209 B2 * 6/2008 Jaccard et al. ........... 250/492.21

FOREIGN PATENT DOCUMENTS

| DE | 10 2005 056 698 A1 | 5/2007 |
| DE | 10 2008 005 068 A1 | 7/2009 |
| EP | 0 864 337 A2 | 9/1998 |
| EP | 1 752 992 A1 | 2/2007 |
| WO | WO 02/07817 A2 | 1/2002 |
| WO | WO 2007/054546 A1 | 5/2007 |

OTHER PUBLICATIONS

German Office Action dated, Feb. 11, 2010.
Particle Detectors / Claus Grupen, BI-Wissenschaftsverlag, 1993.
European Patent Office Action and Search Report dated Mar. 19, 2010 for EP 09169731.8 with English translation.
Safai, Sairos, et al., "Comparison between the lateral penumbra of a collimated double-scattered beam and uncollimated scanning beam in proton radiotherapy," Phys. Med. Biol., vol. 53, 2008, pp. 1729-1750.
Karlsson, M. G., et al., "Electron beam collimation with focused and curved leaf end MLCs-Experimental verification of Monte Carlo optimized designs," Med. Phys., vol. 29, No. 4, Apr. 2002, pp. 631-637.
Karlsson, M. G., et al., "Treatment head design for multileaf collimated high-energy electrons," Med. Phys., vol. 26, No. 10, Oct. 1999, pp. 2161-2167.

* cited by examiner

*Primary Examiner* — Michael Maskell
(74) *Attorney, Agent, or Firm* — Lempia Summerfield Katz LLC

(57) ABSTRACT

The present embodiments relate to lowering the widening of a radiation beam, for example, using a chamber arranged between a beam output and an object to be irradiated. The chamber is filled with a gas or a gas mixture, the average atomic number of which is smaller than that of air, and the volume expansion of which is changeable. The advantage here is that a widening of a radiation beam caused by multiple scattering is reduced.

18 Claims, 4 Drawing Sheets

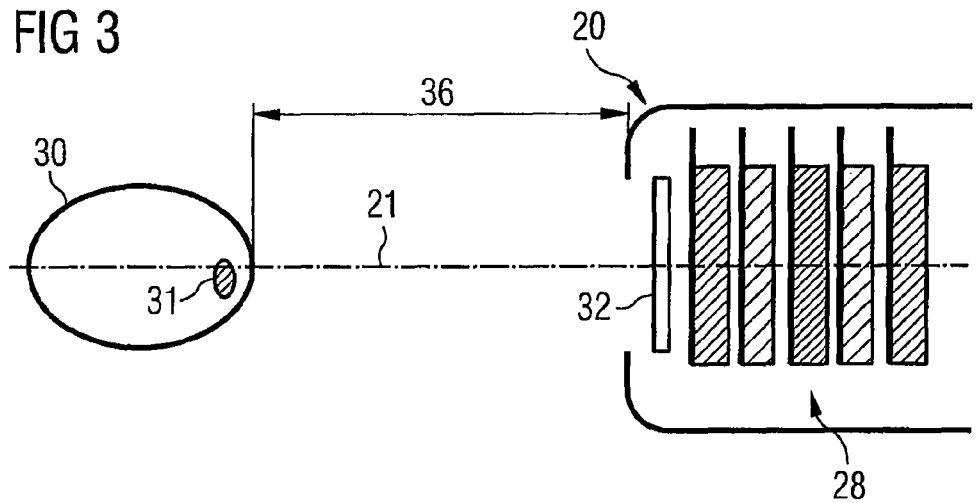
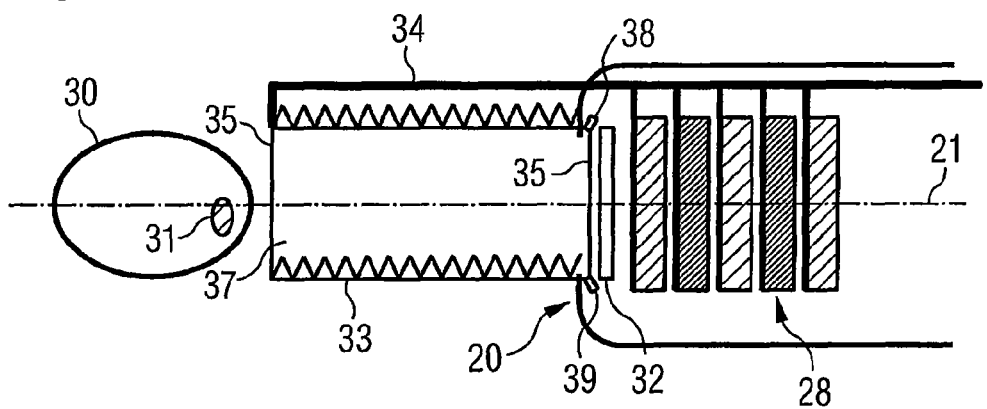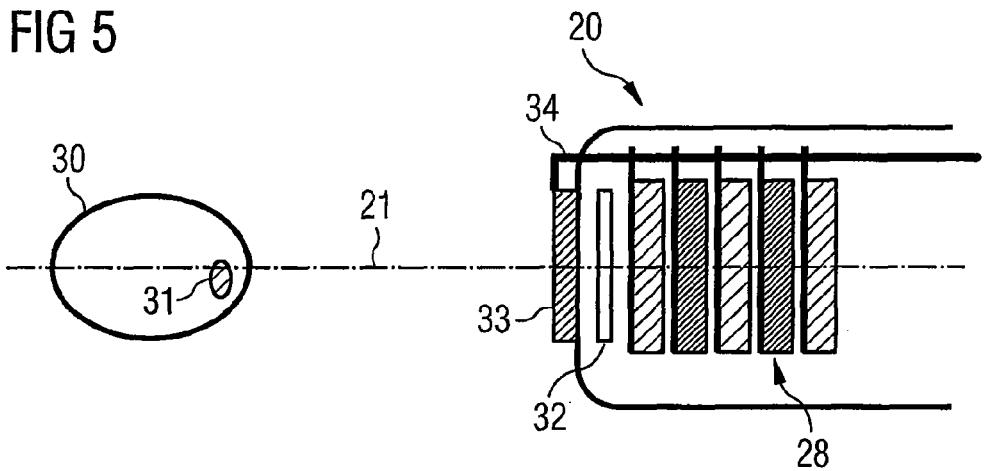

REDUCING THE WIDENING OF A RADIATION BEAM

The present patent document claims the benefit of the filing date of DE 10 2008 058 299.9 filed Nov. 20, 2009, which is hereby incorporated by reference.

BACKGROUND

The present embodiments relate to reducing the widening of a radiation beam in a medical radiation therapy system.

Radiation therapy includes a medical therapeutic method for the treatment of tumor diseases. High-energy photon radiation (e.g., x-ray radiation, gamma radiation) or particle radiation (e.g., electrons, protons, ions) is directed toward an area of the patient's body that is to be treated. However, radiation therapy may be used in non-therapeutic fields, for example when irradiating phantoms or non-living objects in the context of research, or when irradiating materials.

Particle beam therapy includes generating high-energy particle radiation with an acceleration device. The particles accelerated to high energy are formed into a particle beam and subsequently directed toward the tissue to be irradiated. The particles penetrate the tissue to be irradiated and then dissipate their energy into a localized area. The depth of penetration of the particle beam into the tissue to be irradiated is primarily a function of the particle beam's energy. The higher the particle beam's energy, the deeper the particles penetrate into the tissue to be irradiated. In comparison with conventional irradiation methods that work with x-ray and electron beams, particle beam therapy is characterized in that the energy of the particles is dissipated in a localized and distinguishable area. Consequently, in comparison with conventional irradiation methods, a tumor, for example, can be irradiated more precisely, and surrounding tissue can be preserved better.

Particle beam therapy is generally performed in a special particle beam therapy system. In one area of the system, the particle beam is generated and transported to several rooms. In another area, different rooms exist, in which patients are prepared for an upcoming irradiation session or irradiated during an irradiation session.

FIG. 1 shows a schematic overview of a configuration of a particle beam therapy system 1 according to the subsequent publication DE 10 2008 005 068 A1. Ions such as, for example, protons, pions, helium ions or carbon ions are principally used as particles. Particles may be generated in a particle source 2. If, as shown in FIG. 1, two particle sources 2 generate two different types of ions, it is possible to switch between the two types of ions within a short time interval. A switching magnet 3, for example, is used to switch between the two types of ions. The switching magnet 3 is disposed between the ion sources 2 and a pre-accelerator 4. The particle beam therapy system 1 can be operated with protons and with carbon ions simultaneously.

The ions generated by the ion source or one of the ion sources 2 and where applicable selected by the switching magnet 3 are accelerated to a first energy level in the pre-accelerator 4. The pre-accelerator 4 is, for example, a linear accelerator. The particles are then fed into an accelerator 5, for example, a synchrotron or cyclotron. In the accelerator 5, they are accelerated to high energies, such as are required for irradiation. After the particles have exited the accelerator 5, a high-energy beam transport system 6 guides the particle beam to one or more irradiation rooms 7. In an irradiation room 7, the accelerated particles are directed onto a body part that is to be irradiated. The accelerated particles are directed onto the body part from a fixed direction or else from different directions by a rotatable gantry 9 that is movable about an axis 8.

The particle beam therapy system 1 has different rooms 10 in which for example patients are prepared for an upcoming irradiation session or an upcoming examination. These further rooms 10 and the irradiation rooms 7 are connected to one another by corridors.

FIG. 2 shows a schematic overview of the "inner workings" of a proton irradiation system according to EP 0 864 337 A2. After generation and acceleration of a proton beam 21, the cross-sectional dimensions of the proton beam 21 are adjusted by magnet systems 22. A switching unit 23 ensures that the proton beam 21 can be switched off at any time. The proton beam 21 reaches a radiation head 20 or "nozzle". The radiation head 20 includes two deflecting magnets 24, a quadruple magnet 25 that focuses the proton beam 21, an adjusting system 26 that adjusts the energy of the particle beam 21, a collimator lens unit 27 for adjusting the beam form, and a detector system 28 for monitoring the radiation dose dissipated. The proton beam 21 then leaves the radiation head 20 and strikes a patient 30 who is immobilized on a treatment table 29.

When planning medical irradiations, the air gap crossed between beam output and patient is considered, since this gap can cause the widening of a radiation beam as a consequence of multiple scattering.

SUMMARY AND DESCRIPTION

The present embodiments may obviate one or more limitations or drawbacks inherent in the related art. For example, in one or more embodiments, an apparatus and an associated method make it possible to plan more flexibly and more independently of an air gap.

In one embodiment, an apparatus for lowering (i.e., reducing) the widening of a radiation beam is provided. The chamber is arranged between a beam output, for example, a radiation head or "nozzle", and an object to be irradiated. The chamber may be filled with a gas or a gas mixture, the average atomic number of which is smaller than that of air, and the volume expansion of which is changeable. Since multiple scattering in the gas is lower, the beam widens less intensely.

In one embodiment, the chamber may be a hollow body, the length of which is changeable in the direction of the object. Thus the chamber may be adapted for a variable distance to an object.

In one embodiment, the chamber may include a bellows. Accordingly, the chamber may be simple and robust.

The gas may be helium. Helium may be advantageous since it is inexpensive.

In one embodiment, Kapton films may form the two front sides of the chamber, i.e. the sides for the beam input and output. The Kapton films may have no interfering influence on the beam.

In one embodiment, the apparatus includes a radiation head on which the chamber is arranged. Furthermore, the apparatus may include a sliding apparatus. The sliding apparatus may be used to mount the chamber on a radiation head in a safe and easily-operable manner.

In one embodiment, a usage of the apparatus in a medical radiation therapy system, in particular in a particle beam therapy system or an x-ray therapy system, is provided. This offers the advantage that less consideration has to be given in treatment planning to distance-related widening of a radiation beam.

In one embodiment, a method for reducing the widening of a radiation beam is provided. The method may include filling a space between the beam output from a radiation head, and an object to be irradiated, with a gas or a gas mixture, the average atomic number of which is smaller than that of air. The method may include filling the space of a bellows with the gas or the gas mixture. Furthermore the length of the bellows can be changed in the direction of the object. In this way the distance to an object can be bridged easily. The radiation can also be particle radiation or x-ray radiation.

In one embodiment, a usage of the method in a medical radiation therapy system is provided.

BRIEF DESCRIPTION OF THE DRAWINGS

FIG. 3 shows a cross-sectional view of one embodiment of a radiation head with an object to be irradiated, FIG. 4 shows a cross-sectional view of one embodiment of a radiation head with extended bellows, FIG. 5 shows a cross-sectional view of one embodiment of a radiation head with retracted bellows.

DETAILED DESCRIPTION

Figure 1:
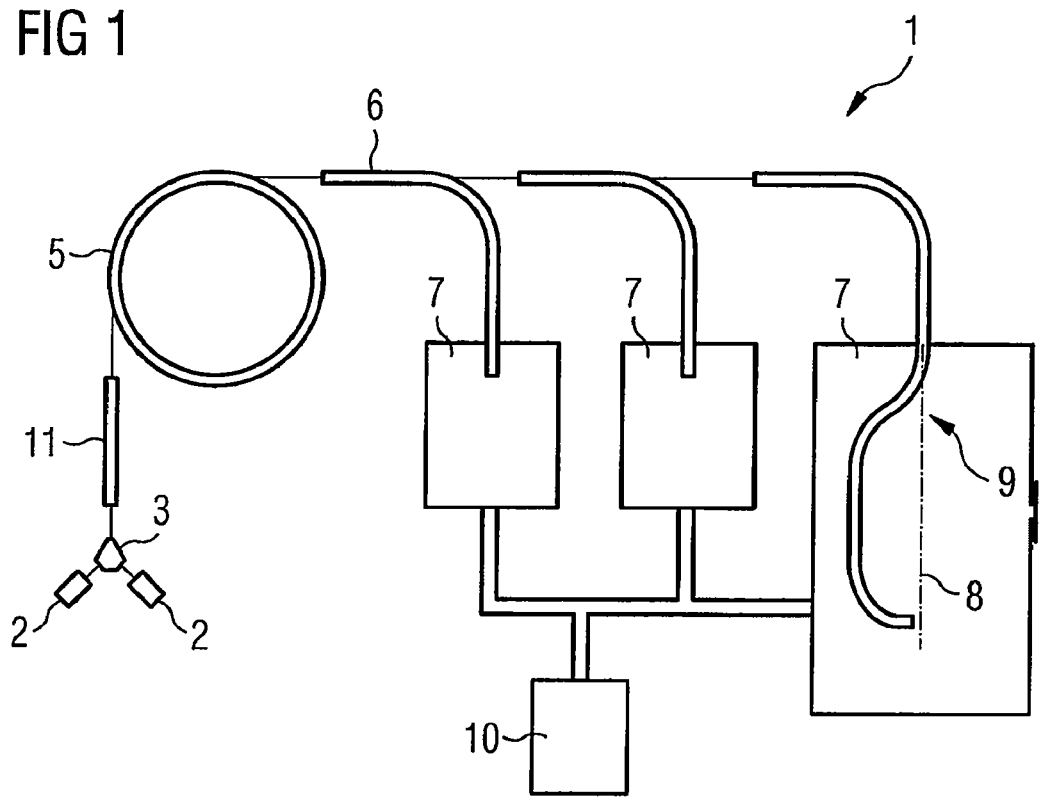
FIG. 1 shows a radiation therapy system according to the prior art.
Figure 2:
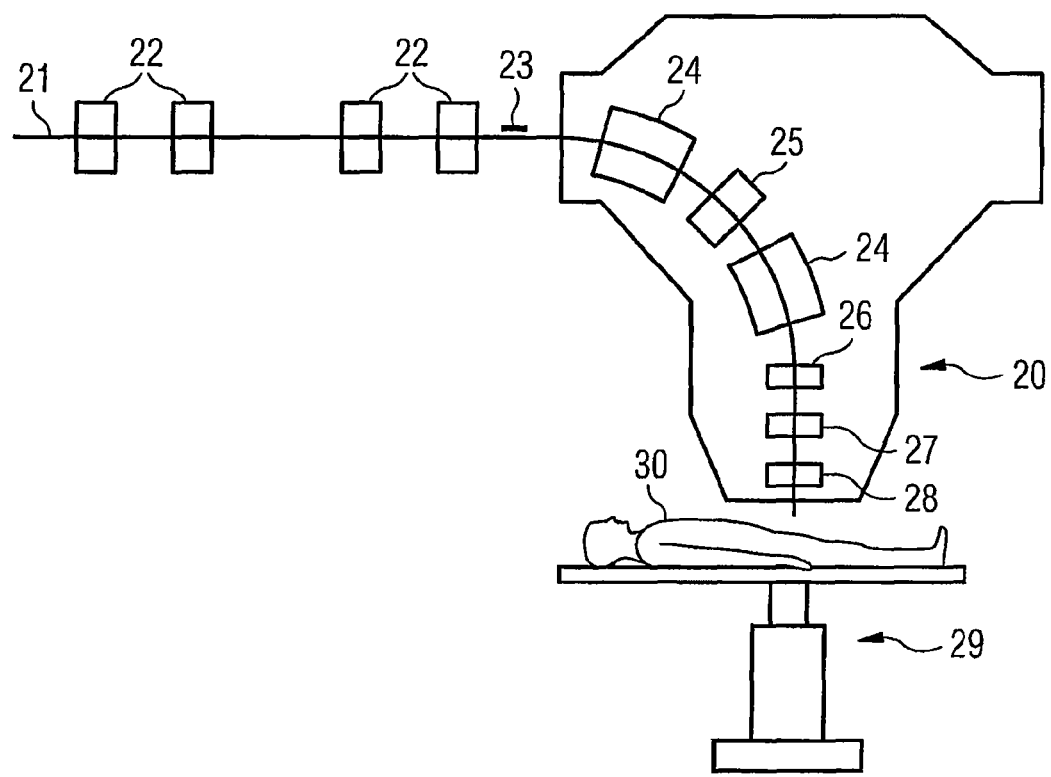
FIG. 2 shows a particle beam therapy system according to the prior art.

The following figures show an apparatus in a particle beam therapy system. The apparatus may be used in other medical and non-medical irradiation systems.

In tumor therapy with ionizing radiation, such as particle radiation, the particles may be generated in a high vacuum and accelerated to high energies. The particles may be protons and/or electrons. In order that the effects of radiation can be deployed in a tumor volume in the body of a patient, the radiation leaves an acceleration apparatus via as thin as possible a vacuum window and cross an air gap, for example, having a length of approximately 1 meter, before the radiation penetrates the patient.

The air gap may be determined by the type of patient support and the focusing of the radiation and thus cannot be changed in any desired manner. The overall treatment planning is based on the unchangeable position of an isocenter. The patient is positioned on a patient support apparatus such that the isocenter is located within the tumor volume.

FIG. 3 shows the relationship described above. The anterior (e.g., front) portion of a radiation head 20 of a particle beam therapy system is shown. The interior of the anterior portion includes a detector system 28 made up of several detectors and a filter unit 32 through which a particle beam 21, for example, a proton beam, passes. After leaving the radiation head 20 the particle beam 21 crosses an air gap 36 before penetrating a patient 30 and there striking a tumor 31. The particle beam 21 dissipates its energy in the tumor 31 and can thereby damage and/or destroy cancerous cells. As a consequence of multiple scattering the radiation beam can be caused to widen, a fact which must be taken into consideration in treatment planning.

When charged particles penetrate a medium they are scattered by the Coulomb potential of the nuclei and electrons. A large number of small scatterings take place with minor deflection. The scattering angle distribution for Coulomb scattering is described by the Moliere theory. From "Particle Detectors/Claus Grupen, BI-Wissenschaftsverlag, 1993" the average scattering angle $\Theta$ is $$\theta = \frac{13.6 \text{ MeV}}{\beta cp} z \sqrt{\frac{x}{X_0}} \left[1 + 0.038 \ln\left(\frac{x}{X_0}\right)\right], \quad (1)$$

where p (in MeV/c) is the momentum, $\beta c$ is the velocity and z is the charge of the scattered particle. $x/X_0$ is the thickness of the scattering medium in units of the radiation length:

$$X_0 = \frac{A}{4\alpha N_A Z^2 r_e^2 \ln\left(183 \cdot Z^{-\frac{1}{3}}\right)}, \quad (2)$$

where Z and A are the atomic number and the atomic weight of the absorber respectively, a is the fine-structure constant, $r_e$ is the classical electron radius and $N_A$ is the Avogadro constant.

Figure 6:
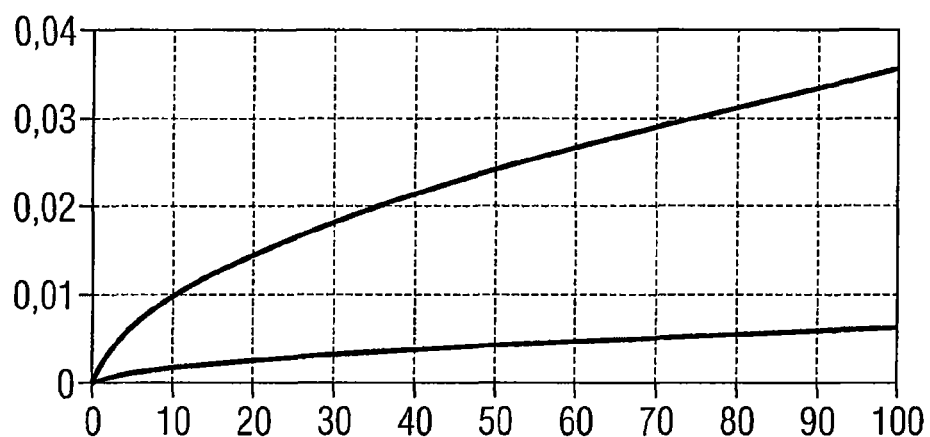
FIG. 6 shows a diagram of the average scattering angle for air and helium.

For protons with an energy of 50 MeV, substituting the material data for air in the equations (1) and (2) produces a dependency of the average scattering angle $\Theta$ in rad as a function of the air gap x in cm as shown in the curve A according to FIG. 6. For small angles the average widening of the beam is found by approximation by multiplication of the average scattering angle $\Theta$ in rad by the gap x. Approximately 35 mm is found for 100 cm from the curve A of FIG. 6.

In one embodiment, at least a portion of the air between the radiation head and the patient is replaced with a noble gas, for example, helium, or with a noble gas mixture, since the average scattering angle is smaller for elements with a low atomic number and low density. In one embodiment, the noble gas is contained in a bellows 33 according to FIGS. 4 and 5.

In FIG. 4 the anterior portion of a radiation head 20 of a particle beam therapy system is shown. The interior of the anterior portion may include a detector system 28 made up of several detectors and a filter unit 32 through which a particle beam 21, for example a proton beam, passes. After leaving the radiation head 20 the particle beam 21 passes through an extended bellows 33 before penetrating a patient 30 and there striking a tumor 31. The particle beam 21 dissipates its energy in the tumor 31 and can thereby damage and/or destroy cancerous cells. The bellows 33 is filled with helium and sealed at its front sides with Kapton films 35. Helium enters the interior 37 of the bellows 33 via an inlet valve 38. Helium can escape from the bellows 33 via an outlet valve 39 if required. Input and output feeds, as well as sensors and a control unit, regulate the supply and removal of the helium depending on the extension capacity of the bellows 33. With the aid of an adjusting unit 34 the required length of the bellows 33 can be set. The length is determined essentially by the distance of the patient 30 to the beam output from the radiation head 20.

In FIG. 5, the bellows 33 is shown in a retracted position in accordance with FIG. 4. In FIG. 5 the anterior portion of a radiation head 20 of a particle beam therapy system is shown. The interior of the anterior portion can include a detector system 28 made up of several detectors and a filter unit 32 through which a particle beam 21, for example a proton beam, passes. After leaving the radiation head 20 the particle beam 21 passes through a retracted bellows 33 before penetrating a patient 30 and there striking a tumor 31. The particle beam 21 dissipates its energy in the tumor 31 and can thereby damage and/or destroy cancerous cells.

Figure 7:
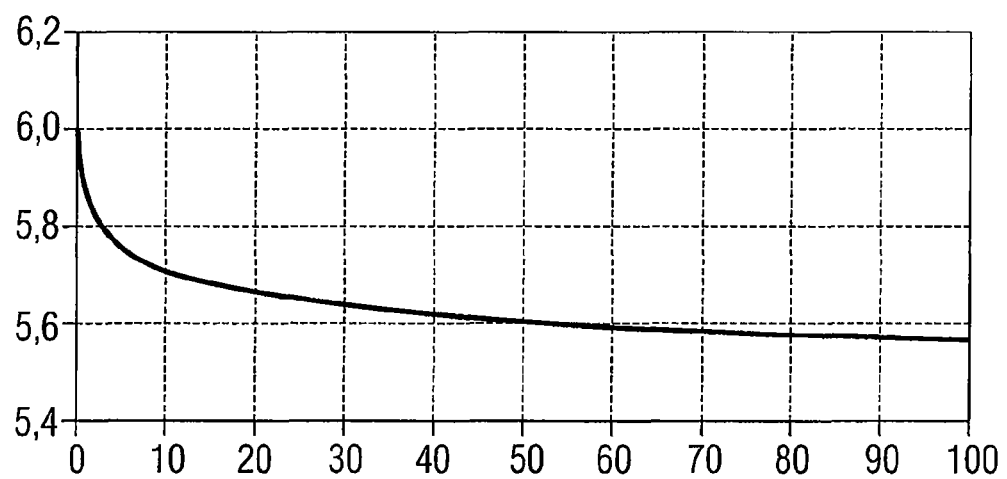
FIG. 7 shows a diagram of the quotient of the average scattering angle for air and helium.

With the aid of the equations (1) and (2) the average scattering angle Θ can be determined for helium. For protons with an energy of 50 MeV, the curve B in FIG. 6 shows the dependency of the average scattering angle Θ in rad as a function of the helium gap x in cm. For small angles the average widening of the beam is found by approximation by multiplication of the average scattering angle Θ in rad by the gap x. Approximately 6 mm is found for 100 cm from the curve B of FIG. 6. Thus a reduction of the average scattering angle Θ by a factor of around 5 to 6 can be produced as a function of the gap x passed through. In FIG. 7 this ratio is shown as a curve C as a function of the length x in cm.

Analogously the widening of a beam of photon radiation, in particular of x-ray radiation, can also be reduced.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. An apparatus for reducing the widening of a radiation beam, the apparatus comprising:
    a bellows arranged between a beam output and an object to be irradiated, wherein the bellows is configured to be filled with a gas or gas mixture having an average atomic number smaller than that of air and a changeable volume expansion; and
    an adjustment unit coupled to the bellows and configured to adjust a length of the bellows in a direction of the radiation beam.

2. The apparatus as claimed in claim 1, wherein the bellows is configured to be filled with the gas, and wherein the gas is helium.

3. The apparatus as claimed in claim 1, wherein the bellows has two sides, and wherein the apparatus further comprises two Kapton films that form the two sides of the bellows.

4. The apparatus as claimed in claim 1, further comprising a radiation head on which the bellows is arranged.

5. The apparatus as claimed in claim 1, wherein the radiation beam is used in a medical radiation therapy system.

6. A method for reducing the widening of a radiation beam, the method comprising:
    positioning a bellows in a space between a beam output of a radiation head and an object to be irradiated;
    filling the bellows with a gas or a gas mixture having an average atomic number smaller than that of air; and
    changing a length of the bellows in a direction of the object.

7. The method as claimed in claim 6, wherein the bellows is filled with the gas, and wherein the gas is helium.

8. The method as claimed in claim 6, wherein the radiation is particle radiation or x-ray radiation.

9. The method as claimed in claim 6, wherein the radiation beam is used in a medical radiation therapy system.

10. The apparatus as claimed in claim 1, wherein the bellows has two sides, and wherein the two sides are a beam input side and a beam output side.

11. The apparatus as claimed in claim 5, wherein the medical radiation therapy system is a particle beam therapy system or an x-ray therapy system.

12. The apparatus as claimed in claim 1, wherein the bellows comprises an inlet valve configured to receive the gas or gas mixture for entry into the bellows.

13. The apparatus as claimed in claim 1, wherein the bellows comprises an outlet valve configured to allow the gas or gas mixture to exit the bellows.

14. The apparatus as claimed in claim 1, wherein the bellows comprises an inlet valve and an outlet valve, the inlet valve configured to receive the gas or gas mixture for entry into the bellows, and the outlet valve configured to allow the gas or gas mixture to exit the bellows, and wherein the bellows further comprises a sensor and a control unit configured to regulate the entry of the gas or gas mixture through the inlet valve and the exit of the gas or gas mixture through the outlet valve.

15. The method as claimed in claim 6, further comprising supplying the gas or the gas mixture to the bellows through an inlet valve on the bellows.

16. The method as claimed in claim 6, further comprising removing the gas or the gas mixture from the bellows through an outlet valve on the bellows.

17. The method as claimed in claim 6, further comprising:
    supplying the gas or the gas mixture to the bellows through an inlet valve on the bellows;
    removing the gas or the gas mixture from the bellows through an outlet valve on the bellows; and
    regulating the supplying and removing of the gas or the gas mixture using a sensor and a control unit.

18. The method as claimed in claim 6, further comprising passing the radiation beam from the beam output of the radiation head through the gas or the gas mixture in the bellows.

* * * * *